(12) United States Patent
Grimard et al.

(10) Patent No.: US 10,213,616 B1
(45) Date of Patent: Feb. 26, 2019

(54) LIGHT THERAPY DEVICE

(71) Applicant: Sun LifeLight, Inc., Beverly, MA (US)

(72) Inventors: Gary D. Grimard, Pelham, NH (US); Alison C. Todd, Manchester, MA (US)

(73) Assignee: Sun LifeLight, Inc., Beverly, MA (US)

( * ) Notice: Subject to any disclaimer, the term of this patent is extended or adjusted under 35 U.S.C. 154(b) by 548 days.

(21) Appl. No.: 14/509,358

(22) Filed: Oct. 8, 2014

Related U.S. Application Data (60) Provisional application No. 61/888,238, filed on Oct. 8, 2013.

(51) Int. Cl.
*A61N 5/06* (2006.01)

(52) U.S. Cl.
CPC ........ *A61N 5/06* (2013.01); *A61N 2005/0658* (2013.01)

(58) Field of Classification Search
CPC .............. A61N 5/06; A61N 2005/0658; A61N 2005/0652; A61N 2005/0663
USPC .......................................................... 607/88
See application file for complete search history.

(56) References Cited

U.S. PATENT DOCUMENTS

| | | | | |
|---|---|---|---|---|
| 6,554,439 B1 * | 4/2003 | Teicher | ................... | F21S 8/006 315/360 |
| 8,620,451 B2 * | 12/2013 | Kennedy | .............. | A61N 5/0616 607/101 |
| 9,032,576 B2 * | 5/2015 | Zelickson | .............. | A46B 13/02 15/22.1 |
| 2005/0065503 A1 * | 3/2005 | Anderson | ............ | A61B 18/203 606/9 |
| 2008/0091250 A1 * | 4/2008 | Powell | ................. | A61M 21/00 607/90 |
| 2008/0275533 A1 * | 11/2008 | Powell | ................. | A61N 5/0616 607/88 |
| 2009/0240311 A1 * | 9/2009 | Andersen | .............. | A61M 21/00 607/90 |
| 2010/0121419 A1 * | 5/2010 | Douglas | ............... | A61N 5/0616 607/90 |
| 2010/0274329 A1 * | 10/2010 | Bradley | ................. | A61N 1/328 607/90 |
| 2012/0206050 A1 * | 8/2012 | Spero | ....................... | B60Q 1/04 315/152 |
| 2013/0301034 A1 * | 11/2013 | Olds | .................... | A61N 5/0618 356/51 |
| 2013/0310903 A1 * | 11/2013 | Li | ......................... | A61N 5/0618 607/88 |
| 2014/0257439 A1 * | 9/2014 | Douglas | ............... | A61N 5/0618 607/90 |

(Continued)

*Primary Examiner* — Gary Jackson
*Assistant Examiner* — Zahed Kabir
(74) *Attorney, Agent, or Firm* — Cesari & McKenna, LLP; Omar M. Wadhwa (57) ABSTRACT

A light therapy device is provided that emits both blue spectrum wavelength light and cyan spectrum wavelength light stimulate intrinsically photosensitive Retinal Ganglion Cell (ipRGC) receptors located in a human eye. The light therapy device may be attached or secured in an area of or directly to a consumer device, such as a computer, or laptop, etc., so that a user operating the consumer device may utilize the consumer device and the light therapy device at the same time. Further, settings of the light therapy device may be controlled utilizing an application that may be executing on a computing device.

18 Claims, 6 Drawing Sheets

(56) References Cited

U.S. PATENT DOCUMENTS

2015/0173151 A1* 6/2015 Ter Weeme ........ H05B 33/0863
315/294

* cited by examiner

LIGHT THERAPY DEVICE

RELATED APPLICATION

The present application claims priority from Provisional Patent Application No. 61/888,238, entitled Light Therapy Device, filed on Oct. 8, 2013, the contents of which are incorporated herein by reference.

BACKGROUND OF THE INVENTION

Field of the Invention

The present application relates to a light therapy device, and more specifically to a user-friendly light therapy device configured to emit light at particular wavelengths.

Background Information

The effects of both light and depression have physical manifestations in the human body. Typically, in the spring and summer months, the human body naturally inhibits the production of melatonin due to the fact that the body is exposed to more natural lighting during the day. In the fall and winter months, the body tends to produce more melatonin due to the shorter days. The increase of melatonin causes a decreased level of serotonin in the body, low levels of serotonin can negatively impact a person's mood/mental state, metabolism, sleep patterns, circadian clock, etc.

Light therapy is a technique to treat mood disorders, such as Seasonal Affective Disorder (SAD), and is specifically designed to have a direct impact on serotonin and melatonin levels in the human body. Specifically, a light therapy device, such as "light boxes", increase the body's production of serotonin and mitigate the effects of melatonin, and as such have a positive effect on a person's mood and/or mental state.

SUMMARY OF THE INVENTION

In an illustrative embodiment, a light therapy device emits light to stimulate Intrinsically Photosensitive Retinal Ganglion Cell (ipRGC) receptors located in a human eye. Specifically, the exemplary light therapy device emits high intensity photons at precise blue spectrum wavelengths (e.g., approximately 475 nm-500 nm) and cyan spectrum wavelengths (e.g., approximately 500 nm-525 nm) to activate the ipRGC receptors, while at the same time minimizing the effects on the rods and cones utilized for normal vision. This is accomplished through utilization of nearly 15,000 lux of photonic energy, while providing less than 1500 lux worth of visual energy. Advantageously, the light therapy device provides maximum therapeutic intensity, while also minimizing the normal side effects experienced with high brightness, such as, headaches, dizziness, and nausea.

The illustrative light therapy device may be attached or secured in an area of or directly to a consumer device, such as a computer, laptop, etc., so that a user operating the consumer device may utilize the consumer device and the light therapy device at the same time. Further, settings and the operation of the light therapy device may be controlled utilizing an application, including one or more graphical user interfaces (GUIs), that may be executing on a computing device such as a desktop computer, a laptop, a tablet, a mobile phone, etc. For example, such aspects may include, but are not limited to, wavelength selection of the blue light and/or cyan light, the intensity of the light, a timer to enable accurate dosage delivery, automatic shutoff with user override, independent user log-on for multi-user workstations, a dosage calculator, etc. that is operatively interconnected to the light therapy device.

BRIEF DESCRIPTION OF THE DRAWINGS

The above and further advantages of the invention may be better understood by referring to the following description in conjunction with the accompanying drawings in which like reference numerals indicate identical or functionally similar elements.

DETAILED DESCRIPTION OF AN ILLUSTRATIVE EMBODIMENT

Figure 1:
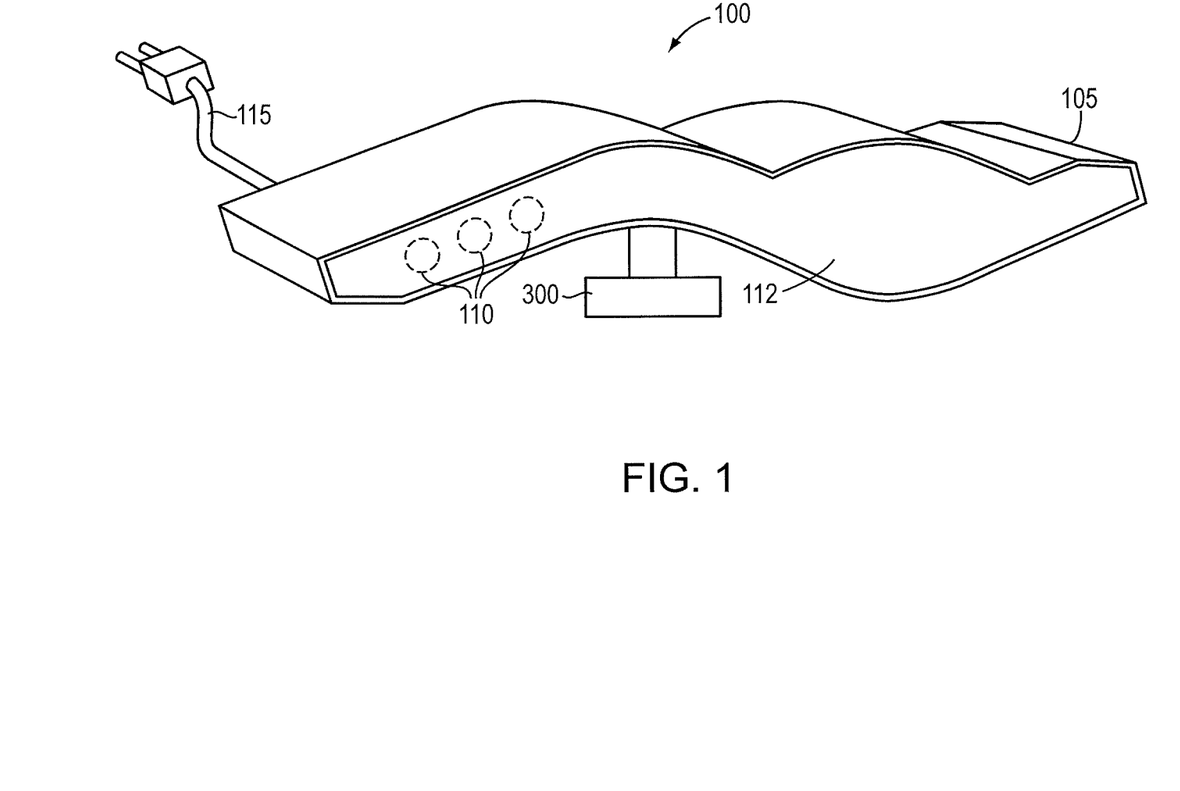
FIG. 1 depicts an example light therapy device.

FIG. 1 depicts a view of an example light therapy device 100. Light therapy device 100 may include a casing 105. The casing 105 illustratively houses the circuitry utilized to illuminate one or more light-emitting diodes (LEDs) 110, as seen as dotted spheres, that provide high intensity photons at precise blue spectrum wavelengths (e.g., approximately 475 nm-500 nm) and cyan spectrum wavelengths (e.g., approximately 500-525 nm), to stimulate Retinal Ganglion Cell (ipRGC) receptors located in a human eye. Further, casing 105 may include a transparent portion 112 that protects the LEDs 110, but also allows the light emitted from the LEDs 110 to reach the human's eye. For example, the transparent portion 112 may be a lens that blends blue light and cyan light provided by the one or more LEDs 110. In alternative embodiments, the transparent portion may not blend the blue and cyan light, but instead simply allow the blue light and cyan light to be distinct as they emit through the transparent portion 112. In one embodiment, the LEDs, shown as the dotted spheres, cannot be seen through transparent portion 112, and only the light emitted from the LEDs 110 may be seen. Light therapy device 100 may have one or more power supplies such as a power cord 115 that may be plugged into an outlet (not shown) to provide power to the LEDs 110. In alternative embodiments, batteries (not shown) may be used in conjunction with or in place of the power cord 115.

Figure 3:
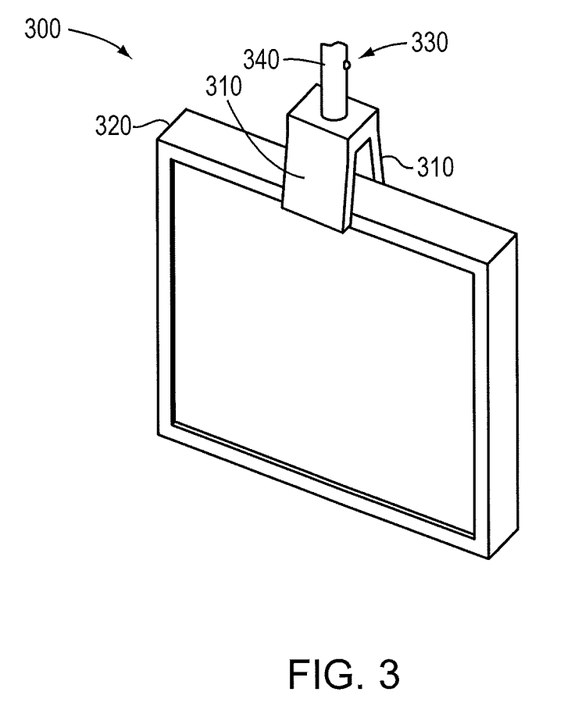
FIG. 3 depicts an example mount that may be utilized to secure the light therapy device in an area of or directly to a consumer device or object.

Light therapy device 100 may further include a mount 300 that may be utilized to secure the light therapy device 100 in an area of or directly to a consumer device, such as a laptop or desktop. Specifically, a user may utilize the mount 300 to position and secure the light therapy device 100 at a particular location, thus allowing the user to move and secure the light therapy device at any location where the user desires. For example, the user may utilize the mount 300 to secure the light therapy device 100 on the top of a monitor, so that the light emitted from LEDs 110 is angled at a downward direction and towards the ipRGC receptors located in a human eye. For example, a user operating a computer, may, at the same time, also utilize light therapy device 100. Advantageously, the user may receive the benefits associated with blue and cyan light provided by the light therapy device 100 to stimulate the user's iPRGC receptors while the user is working/using his computer. In alternative embodiments, the light therapy device may utilize the mount 300 to secure the light therapy device 100 to a desk, a wall partition, or any other device/structure. It is noted that light therapy device 100 may be of any shape and size, and the shape and size of light therapy device 100 as depicted in FIG. 1 is simply exemplary in nature.

Figure 2:
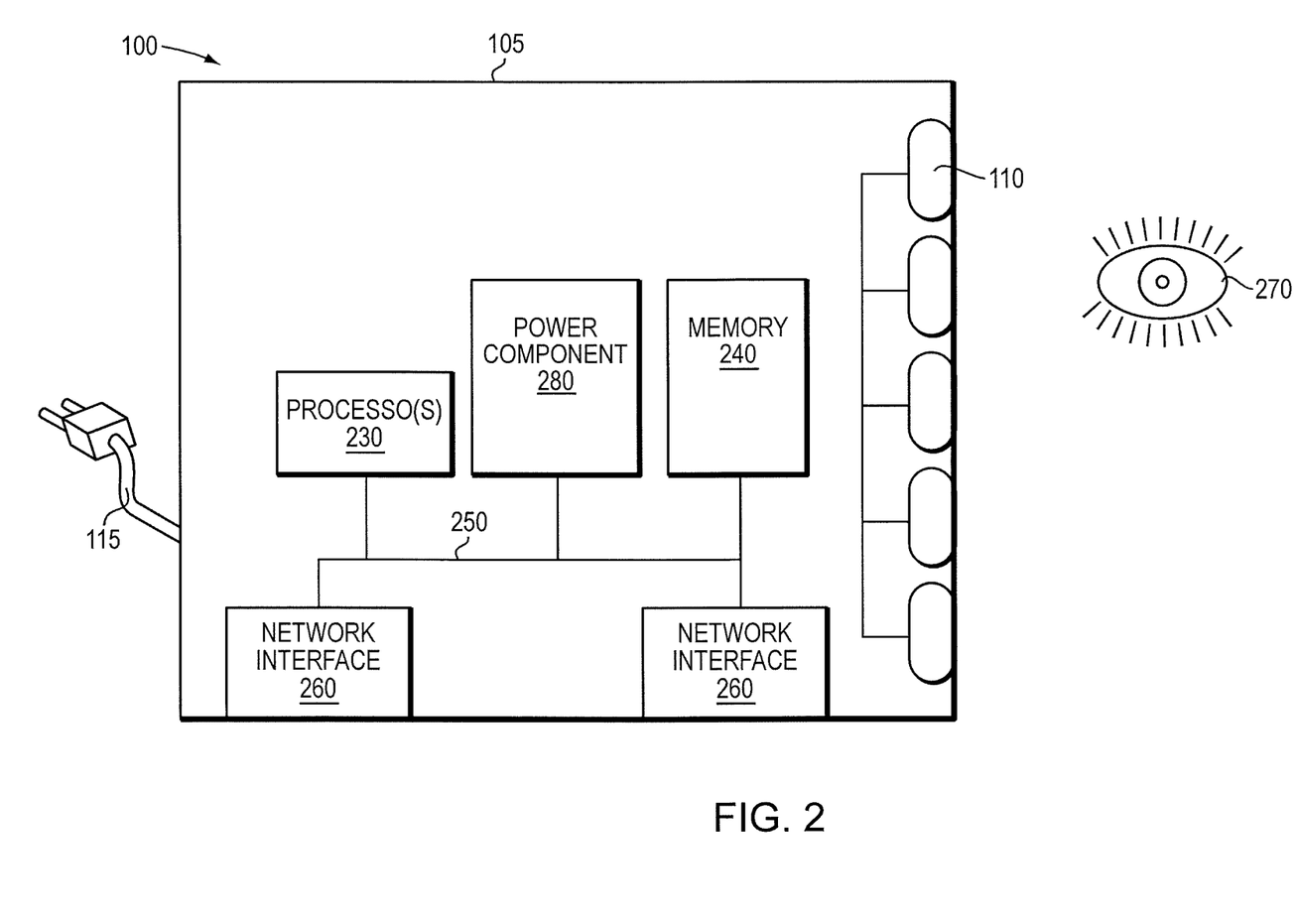
FIG. 2 depicts an example light therapy device and its components.

FIG. 2 depicts an example light therapy device 100 and its components. Light therapy device 100 may include one or more network interfaces 260, one or more processors 230, a memory 240, and a power component 280 interconnected by a system bus 250, for example. The network interfaces 260 may contain the mechanical, electrical, and signaling circuitry for communicating data over physical links or over a wireless network, as known by those skilled in the art. The network interfaces 260 may be configured to transmit and/or receive data using a variety of different communication protocols. The one or more processors 230, for example, may receive instructions from a processor of a computing device that is executing an application utilized to control the settings and operation of the light therapy device 100 and LEDs 110, as described in more detail below, to stimulate the user's iPRGC receptors in a human eye 270. The memory 240, for example, may be utilized to store one or more instructions or logic signals received to control light therapy device 100. Further, it is noted that LEDS 110 are shown as spheres in FIG. 2, but may be any shape and size.

The memory 240 comprises a plurality of locations that are addressable by the processor(s) 230 and the network interfaces 260 for storing software programs and data structures associated with the embodiments described herein. The processor(s) 230 may comprise necessary elements or logic adapted to execute software programs and manipulate data structures associated with the settings and the operation of the light therapy device 100, and specifically so LEDs 110 may be illuminated by the processor, for example. More specifically, power from an outlet (not shown) may be provided through power cord 115, to power component 280 to illuminate one or more LEDs 110, wherein the manner in which the LEDs 110 are illuminated are dictated by the processor(s) 230. Moreover, it is noted that the network interfaces, the one or more processors, memory, and system bus (similar to the circuitry to illuminate the one or more LEDs 110) are internal to the casing 105.

FIG. 3 depicts a view of an exemplary mount 300, that may for example, be utilized to secure the light therapy device 100 to a consumer device or object 320. Mount 300, includes one or more platforms 310 that are utilized to secure the mount 300 to a consumer device or object 320. The consumer device or object 320 may be, but are not limited to, a monitor of a desktop computer, a desk or table top, a shelf, a wall/divider, partition, etc. Further, each platform 310 may be made of any type of material, such as plastic, aluminum, etc. Moreover, each platform 310 may be configured to move in one or more directions, so that two or more platforms 310 may be tightened or secured around the consumer device or object 320. The movement of the one or more platforms may be achieved through the use of springs, or other mechanisms as known by those skilled in the art. For example, platforms 310 may be placed on either side of a monitor of a desktop computer, and pressed/clamped to make secure contact with the consumer device or object 320, wherein the one or more platforms may then be secured at that position to firmly secure the mount 300 to the consumer device or object 320. It is noted that although two platforms of a specific size relative to consumer device or object 320 are shown in FIG. 3, it is expressly contemplated that any number of platforms 310 having any size and shape may be utilized.

Further, mount 300 may be attached to the light therapy device 100 in a variety of ways. For example, a screw 300, or other securing device may be utilized to attach, an appendage 340 of the mount 300, to light therapy device 100. For example, the screw 300 may be positioned to travel through a hole of the appendage 340, and fastened to the backside of the light therapy device 100. Advantageously, the mount 300 and light therapy device may be dis-attached and moved to different locations independently. For example, a user may want to travel to different locations and carry simply the light therapy device 100 and/or the mount 300. Alternatively, mount 300 may remain attached to light therapy device 100, and the attached devices may be transported together to locations.

Figure 4:
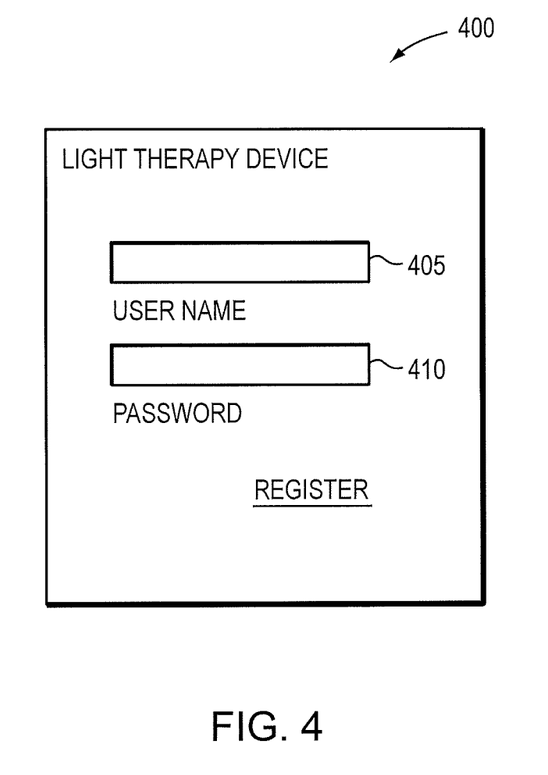
FIG. 4 is an example GUI Login window associated with an application that may be utilized in conjunction with light therapy device.

FIG. 4 is a screenshot of an exemplary GUI window 400, that may for example, be associated with an application that may be utilized in conjunction with light therapy device 100. Specifically, window 400 may include a log in option that allows a user, who wants to utilize light therapy 100, to provide a username at field 405 and password at field 410 to access the application and his/her personal settings associated with light therapy device 100. For example, and as known by those skilled in the art, a user may register by providing his/her name, address, email address, and/or other personal information in signing up or registering with the application to obtain a username and password to access setting associated with the light therapy device. Thereafter, the user may utilize the window 400 as shown in FIG. 4 to enter his/her username and password.

It is noted that the application may be user independent. For example, two different users may access their own respective settings, by providing their username and password. Advantageously, two users that utilize the same desktop computer, at different times, may access their settings and control the light therapy device that is attached to the desktop computer. For example, a first user may work at a company from 9 am-3 pm, and may control the settings and operation of the light therapy device owned by the company and attached to a desktop computer, by the first user logging into his/her account through the application on the desktop computer. A second user may also work at the company but from 4 pm-12 am, and may control the settings and operation of the light therapy device owned by the company by logging into his/her account through the application on the desktop computer.

Figure 5:
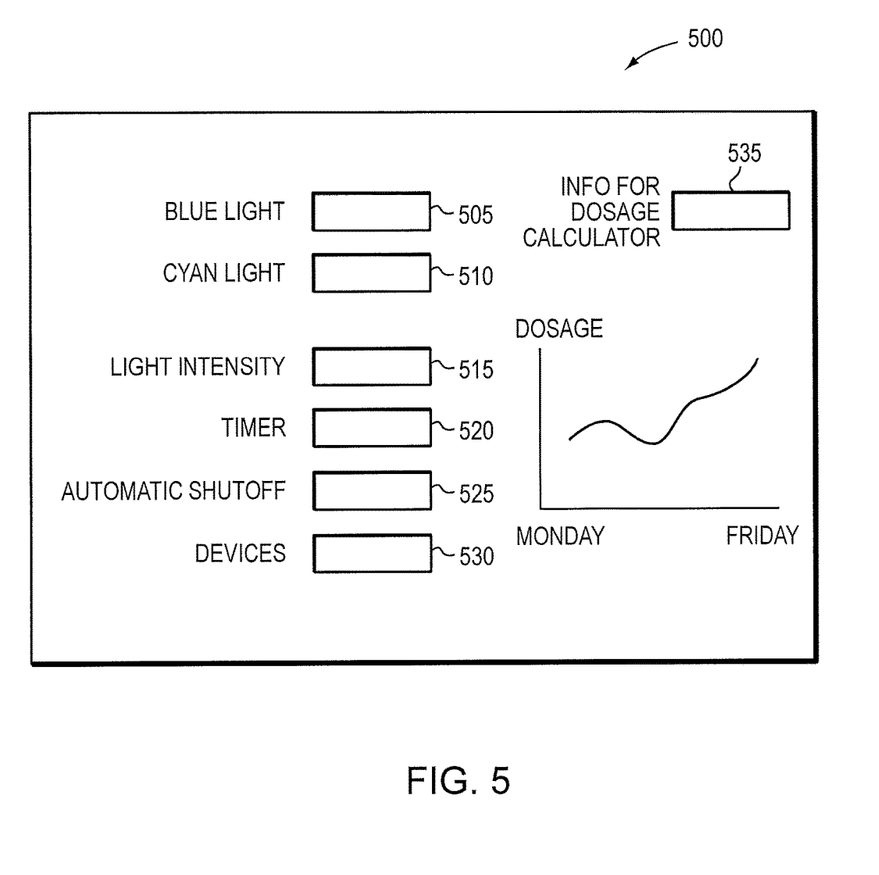
FIG. 5 is an example GUI window associated with an application that may be utilized in conjunction with light therapy device.

FIG. 5 is an example GUI window 500, that may for example, be associated with an application that may be utilized in conjunction with light therapy device after a user has logged in as described with reference to FIG. 4. Specifically, the window 500 as shown in FIG. 5 allows a user to input one or more commands associated with the settings and the operation of the light therapy device 100. Specifically, the user may utilize the window 500 as shown in FIG. 5 to ensure the light therapy device 100 operates in a manner that the user desires. For example, the user may utilize one or more fields to alter the settings and operation of the light therapy device 100. Specifically, one or more fields 505 and one or more fields 510 may be utilized by the user to respectively indicate the specific wavelengths that the light therapy device should output the blue light and/or cyan light.

For example, a user may indicate that the light therapy device 100 should output or provide the blue light at 490 nm and cyan spectrum at 515 nm. Further, the user may utilize one or more field 515 to indicate the intensity of the one or more LEDs 110 of the light therapy device. For example, the user may utilize the fields 515 to indicate how bright the one or more LEDs 110 should be illuminated.

One or more fields 520, may be utilized by the user to set or alter a time associated with the light therapy device to enable accurate dosage of light delivery. For example, the user may utilize a calendar associated with the one or more field 520, or some other depiction, that allows the user to enter information within one or more fields 520 to set a schedule for the light therapy device. For example, the user may use the one or more fields 520 to indicate that the light therapy should be turned on and operational for a certain time range on Mondays, or Tuesdays, or during a specific month, or season, etc. Advantageously, the settings of the light therapy device 100 can be configured to operate according to when the user desires, and can be powered automatically based on the conditions set in one or more fields 520.

One or more fields 525 may be utilized for an automatic shutoff with user override, that may allow the user the ability to turn the light therapy device 100 off at a certain time, or after the light therapy device has been operating for a certain amount of time. However, if the user has indicated that the light therapy device 100 should in fact operate for a duration longer than indicated by the automatic shutoff, the automatic shutoff as indicated in one or more fields 525 may be overridden. For example, if the user indicates in fields 520 that the light therapy device should operate on Mondays from 9 am-12 pm, and the one or more fields 525 indicate that the light therapy device should only be on for 2 hours, the settings in one or more fields 520 will override the settings in fields 525.

One or more fields 530 may allow the user to indicate what other devices should be allowed to access the application to control the light therapy device. For example, a user may own a plurality of devices, such as desktop computer at work and a desktop computer at home, that he/she would like to access the application to control the operation of the light therapy device and ensure that changes made at one location are accessible at the other location. Using fields 530, the user may indicate what devices should be able to access the settings associated with the light therapy device. Thus, the user may access the application, associated with the light therapy device, utilizing the desktop computer at home and/or at work and be able to access updated settings regardless of what device was utilized to enter or update the settings.

Further, one or more fields 535 may be utilized by the user to allow the user to access a dosage calculator and obtain statistics regarding the dosage of light the user has been provided by the light therapy device 100 over a period of time. For example, the one or more fields 535 may be a time range or some other variable the user may be able to control, to obtain output data 540 regarding the light therapy device and the amount of light, wavelengths, intensity, etc., that the user has been exposed to for the time range.

Further, it is noted that although reference is made to a single GUI interface of FIG. 5 to enable the user to input commands to control the setting and the operation of the light therapy device, a plurality of GUIs may be utilized. Further, although reference is made to particular settings as shown in the GUI of FIG. 5, other settings, as known by those skilled in the art and associated with a light therapy device, may be controlled by the application as described herein. Furthermore, although reference to FIG. 5 is made with the user inputting certain information in the fields, it is expressly contemplated that the user may, in alternative embodiments, select values from drop-down menus, or provide information to the application in a variety of different ways as known by those skilled in the art.

Figure 6:
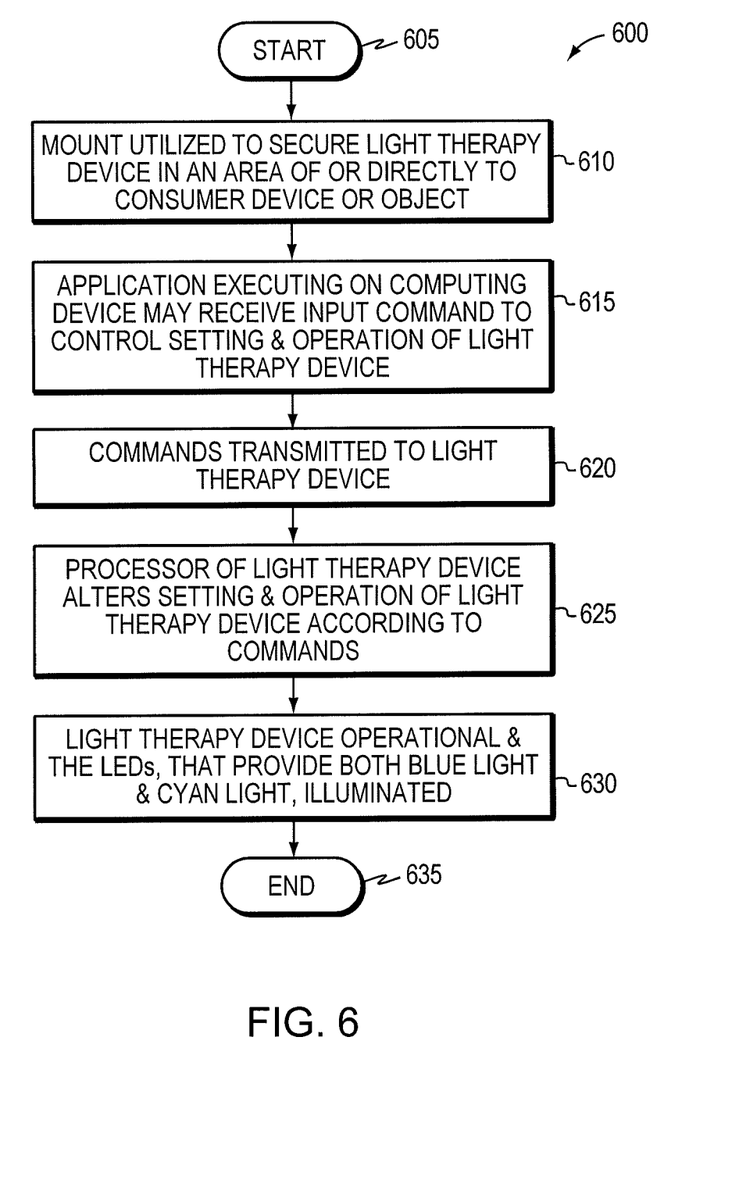
FIG. 6 is a flowchart detailing the steps of a procedure for the operation of the light therapy device in accordance with an illustrative embodiment of the invention.

FIG. 6 is a flowchart detailing the steps of a procedure 600 for the operation of the light therapy device in accordance with an illustrative embodiment of the invention. The procedure 600 starts at step 605 and continues to step 610, wherein a mount of the light therapy device is utilized to secure or attach the light therapy device in an area of or directly to a consumer device or object. For example, the mount may be utilized to secure the light therapy device to a monitor of a desktop computer. In alternative embodiments, the mount may be utilized to secure the light therapy device to a desk, a wall partition, or any other device/structure. In step 615, an application executing on a computing device having a processor may receive one or more input commands to control settings and operation of the light therapy device. For example, the application may be a mobile application executing on a mobile phone. In an alternative embodiment, the application may be a software application executing on a desktop computer, a laptop, and/or tablet. Further, the input commands may include, but are not limited to, the wavelength selection of the blue light and/or cyan light, the intensity of the light, a timer to enable accurate dosage delivery, automatic shutoff with user override, independent user log on for multi-user workstations, a dosage calculator, etc. For example, a user may input the commands at a command line interface (CLI) using a keyboard or other input device, and/or by utilizing one or more GUIs, indicating that the light therapy device should output (e.g., LEDs should illuminate) the blue light at 490 nm and cyan spectrum at 515 nm, and that the LEDs should illuminate at a certain intensity.

At step 620, the commands or logical instructions associated with the received commands may be transmitted to the light therapy device. For example, the commands or the logical instructions may be sent over a wireless network to a processor of the light therapy device. In alternative embodiments, the commands or logical instructions may be transmitted from the application executing on the computing device to the light therapy device utilizing a cable that couples the computing device executing the application to the light therapy device. A memory of light therapy device may store the instructions. At step 625, the processor of the light therapy alter settings and the operations of the light therapy device in accordance with the commands input by the user. At step 630, light therapy device is operational and the one or more LEDs, that provide both blue light and cyan light, are illuminated according to the user commands to stimulate ipRGC receptors located in a human eye. In step 635, the procedure ends.

The foregoing description described certain example embodiments. It will be apparent, however, that other variations and modifications may be made to the described embodiments, with the attainment of some or all of their advantages. For instance, it is expressly contemplated that the light therapy device may be of any shape and size that is capable of emitting both blue and cyan light. Accordingly, the foregoing description is to be taken only by way of example, and not to otherwise limit the scope of the disclosure. It is the object of the appended claims to cover all such variations and modifications as come within the true spirit and scope of the disclosure.

What is claimed is:

1. A light therapy device, comprising:
   a first set of one or more light-emitting diodes (LEDs) providing blue spectrum wavelength light;
   a second set of one or more light-emitting diodes (LEDs) providing cyan spectrum wavelength light, wherein the first set of one or more LEDs and the second set of one or more LEDs are configured to stimulate intrinsically photosensitive Retinal Ganglion Cell (ipRGC) receptors;
   a casing to house circuitry to illuminate the first and second set of LEDs;
   a mount utilized to secure the light therapy device in an area of or directly to a consumer device;
   a processor of the light therapy device to receive, over a computer network and from an application executing on a computing device, one or more user commands indicating
      at least one of a selected blue wavelength the light therapy device should output the blue spectrum wavelength light during operation and a selected cyan wavelength the light therapy device should output the cyan spectrum wavelength light during operation,
      an intensity of the first set of one or more LEDs and the second set of one or more LEDs during operation,
      a dosage delivery indicating at least a time the first set of one or more LEDs and the second set of the one or more LEDs are to be illuminated during operation, and
      an automatic shutoff indicating at least one of a selected time the first set of one or more LEDs and the second set of one or more LEDs should be off and a maximum amount of time the first set of one or more LEDs and the second set of one or more LEDs should be operational,
         wherein the first set of one or more LEDs and the second set of one or more LEDs are operational according to the dosage delivery and the automatic shutoff is overridden when the time period indicated by the dosage delivery conflicts with the automatic shutoff, and
   the processor configured to illuminate the first set of one or more LEDs that provide the blue spectrum wavelength light and the second set of one or more LEDs that provide the cyan spectrum wavelength light based on the one or more user commands received from the application executing on the computing device over the computer network.

2. The light therapy device of claim 1, wherein the application provides independent user log on for multi-user workstations and a dosage calculator.

3. The light therapy device of claim 1, wherein the consumer device is one of a laptop computer, a desktop computer, a mobile phone, and a tablet.

4. The light therapy device of claim 1, wherein one or more graphical user interfaces (GUIs) are utilized to accept the one or more user input commands.

5. The light therapy device of claim 1, wherein the blue spectrum wavelength light is in a range of 475 nm to 500 nm and the cyan spectrum wavelength light is in a range of 500 nm to 525 nm.

6. The light therapy device of claim 1, wherein the application is a mobile application.

7. The light therapy device of claim 1, further comprising a memory to store the one or more user input commands.

8. A system for operating a light therapy device, the system comprising:
   an application executing on a computing device and configured to receive one or more user input commands associated with the light therapy device, wherein the one or more user commands indicate
      a blue wavelength selection for blue light during operation,
      a cyan wavelength selection for cyan light during operation,
      an intensity of light emitted by the light therapy device during operation,
      a dosage delivery indicating at least a time the light therapy device is to be operational, and
      an automatic shutoff indicating at least one of a selected time the light therapy device should be off and a maximum amount of time the light therapy device should be operational,
         wherein the light therapy device is operational according to the dosage delivery and the automatic shutoff is overridden when the time period indicated by the dosage delivery conflicts with the automatic shutoff;
   a processor, executing on the light therapy device, to receive the one or more user input commands over a computer network from the application executing on the computing device;
   the processor to utilize the one or more user input commands to set the blue light at the blue wavelength selection and set the cyan light at the cyan wavelength selection, the processor to control the intensity of the blue light and the cyan light emitted by one or more light-emitting diodes (LEDs) of the light therapy device; and
   the one or more LEDs of the light therapy device to operate and emit the blue light at the blue wavelength selection and the cyan light at the cyan wavelength selection according to the one or more user input commands received over the computer network, and the one or more LEDs of the light therapy device to further operate the blue light and the cyan light at the intensity according to the one or more user input commands, wherein the one or more LEDs are configured to stimulate intrinsically photosensitive Retinal Ganglion Cell (ipRGC) receptors.

9. The system of claim 8, wherein the blue wavelength is in a range of 475 nm to 500 nm and the cyan wavelength is in a range of 500 nm to 525 nm.

10. The system of claim 8, wherein in the application provides independent user log on for multi-user workstations and a dosage calculator.

11. The system of claim 8, wherein the computing device is one of a laptop computer, a desktop computer, a mobile phone, and a tablet.

12. The system of claim 8, wherein one or more graphical user interfaces (GUIs) are utilized to accept the one or more user input commands.

13. The system of claim 8, wherein the application is a mobile application.

14. The system of claim 8, further comprising a memory to store the one or more user input commands.

15. A system, comprising:
   one or more network interfaces adapted to communicate data over a computer network;
   a processor coupled to a memory and the network interfaces and adapted to execute one or more processes configured to:

receive one or more user commands indicating
a first selected wavelength of blue spectrum wavelength light output during operation of one or more light-emitting diodes (LEDs),
a second selected wavelength of cyan spectrum wavelength light output during operation of the one or LEDs,
a dosage delivery indicating at least a time the one or more LEDs are to be illuminated during operation, and
an automatic shutoff indicating at least one of a selected time the one or more LEDs should be off and a maximum amount of time the one or more LEDs should be operational,
wherein the one or more LEDs are operational according to the dosage delivery and the automatic shutoff is overridden when the time period indicated by the dosage delivery conflicts with the automatic shutoff; and
operate the one or more LEDs to output the blue spectrum wavelength light and the cyan spectrum wavelength light at the first selected wavelength and the second selected wavelength based on the one or more user commands.

16. A system of claim 15, wherein the one or more commands further indicate at least one of an intensity of the LEDs, wherein the one or more user commands are received through an application that provides independent user log on for multi-user workstations and a dosage calculator.

17. A system of claim 15, wherein one or more graphical user interfaces (GUIs) are associated with an application and are utilized to accept the one or more user commands from a user utilizing the system.

18. A system of claim 15, wherein the blue spectrum wavelength light is in a range of 475 nm to 500 nm and the cyan spectrum wavelength light is in a range of 500 nm to 525 nm.

* * * * *